United States Patent
Roy et al.

(12) 
(10) Patent No.: US 6,730,679 B1
(45) Date of Patent: *May 4, 2004

(54) PHARMACEUTICAL FORMULATIONS

(75) Inventors: Arup K. Roy, Greenville, NC (US); Lloyd Gary Tillman, Carlsbad, CA (US)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 236 days.

(21) Appl. No.: 08/820,848

(22) Filed: Mar. 20, 1997

Related U.S. Application Data

(60) Provisional application No. 60/013,893, filed on Mar. 22, 1996.

(51) Int. Cl.$^7$ .................... A61K 31/495; A61K 31/535; A61K 31/47; A61K 31/425
(52) U.S. Cl. .................... 514/255; 514/231.2; 514/307; 514/365; 514/458
(58) Field of Search .............. 514/255, 231.2, 514/307, 365, 458

(56) References Cited

U.S. PATENT DOCUMENTS

| | | | |
|---|---|---|---|
| 5,234,695 A | 8/1993 | Hobbs et al. | 424/498 |
| 5,430,021 A | 7/1995 | Rudnic et al. | 514/14 |
| 5,585,397 A | 12/1996 | Tung et al. | 514/473 |
| 5,744,481 A | 4/1998 | Vazquez et al. | 514/311 |
| 5,786,483 A | 7/1998 | Vazquez et al. | 546/168 |
| 5,830,897 A | 11/1998 | Vazquez et al. | 514/256 |
| 5,843,946 A | 12/1998 | Vazquez et al. | 514/252 |

FOREIGN PATENT DOCUMENTS

| | | | |
|---|---|---|---|
| EP | 0539215 A1 | 4/1993 | |
| EP | 0 810 209 A2 | 12/1997 | ......... C07C/311/05 |
| WO | WO 92/13531 | 8/1992 | |
| WO | WO 94/04492 | 3/1994 | ......... C07C/311/29 |
| WO | WO 95/06030 | 3/1995 | ......... C07C/311/29 |
| WO | WO 95/20384 | 8/1995 | |
| WO | WO 95/31217 | 11/1995 | |
| WO | WO 96/03113 | 2/1996 | |
| WO | WO 96/36316 | 11/1996 | |

OTHER PUBLICATIONS

Kim et al, 122CA: 2085494, 1995.*
Al–Razzak et al 112 CA299083p, 1995.*
Adams, 118CA219619X, 1993.*

* cited by examiner

*Primary Examiner*—Russell Travers
(74) *Attorney, Agent, or Firm*—Marc S. Wiener; Birch, Stewart, Kolasch & Birch

(57) ABSTRACT

Pharmaceutical formulations containing HIV protease inhibitors, specifically including 3S-[3R*(1R*,2S*)]-[3-[[(4-aminophenyl)sulphonyl](2-methylpropyl)-amino]-2-hydroxy-1-phenylmethyl)propyl]carbamic acid, tetrahydro-3-furanyl ester (alternatively known as VX 478 or 141W94), and a tocopherol, and their use in medical therapy are described.

21 Claims, 1 Drawing Sheet

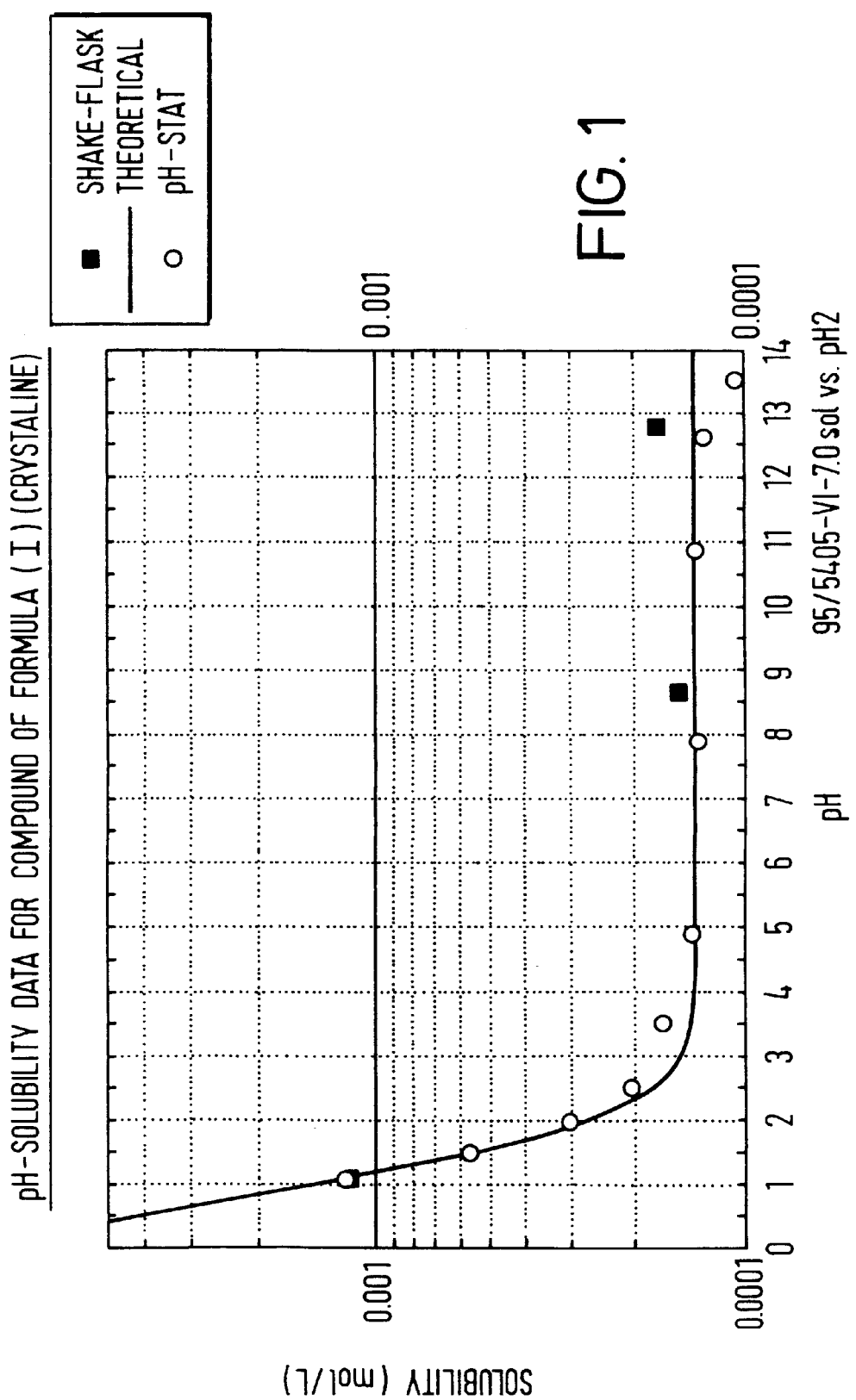

PHARMACEUTICAL FORMULATIONS

This application claims priority from Provisional US Application No. 60/013,893 filed Mar. 22, 1996, which claims prior priority for Great Britain Application No. 9606372.2 filed Mar. 26, 1996.

The present invention relates to novel pharmaceutical formulations containing HIV protease inhibitors, specifically including 3S-[3R*(1R*, 2S*)]-[3-[[(4-aminophenyl)sulphonyl](2-methylpropyl)-amino]-2-hydroxy-1-phenylmethyl)propyl]carbamic acid, tetrahydro-3-furanyl ester (alternatively known as VX 478 or 141W94), and a tocopherol, and their use in medical therapy.

The present invention is within the field of pharmaceutical science, in particular in the area of drug delivery, specifically the delivery of HIV protease inhibitors.

Inhibitors of HIV protease have potent activity against Human Immunodeficiency Virus (HIV), the causative agent of Acquired Immune Deficiency Syndrome (AIDS) and related conditions such as AIDS-related Complex (ARC). Examples of protease-inhibiting compounds include those disclosed in WO94/05639, WO95/24385, WO94/13629, WO92/16501, WO95/16688, WO/US94/13085, WO/US94/12562, US93/59038, EP541168, WO94/14436, WO95/09843, WO95/32185, WO94/15906, WO94/15608, WO94/04492, WO92/08701, WO95/32185, and U.S. Pat. No. 5,256,783, in particular (S)-N-((.alpha.S)-((1R)-2-((3S, 4aS, 8aS)-3-(tert-Butylcarbomoyl)octahydro-2-(1H)-isoquinolyl)-1-hydroxyethyl)phenethyl)-2-quinaldaminosuccinamide monomethanesulfonate (saquinavir), N-(2(R)-Hydroxy-1(S)indanyl)-2(R)-(phenylmethyl)-4(S)-hydroxy-5-[1-[4-(3-pyridylmethyl)-2(S)-(N-tert-butylcarbamoyl)piperazinyl]]pentaneamide (indinavir), 10-hydroxy-2-methyl-5-(1-methylethyl)-1-[2-(1-methylethyl)-4-thiazolyl]-3,6-dioxo-8,11-bis(phenylmethyl)-2,4,7,12-tetraazatridecan-13-oic acid, 5-thiazolylmethyl ester (ritonavir), (N-(1,1-dimethyl)decahydro-2-[2-hydroxy-3-[(3-hydroxy-2-methylbenzoyl)amino]-4-(phenylthio)butyl]-3-isoquinolinecarboxamide monomethanesulfonate (nelfinavir), and related compounds.

In particular 3S-[3R*(1R*, 2S*)]-[3-[[(4-aminophenyl)sulphonyl](2-methylpropyl)-amino]-2-hydroxy-1-phenylmethyl)propyl]carbamic acid, tetrahydro-3-furanyl ester; [3-(S)-N-(3-tetrahydrofuranyloxycarbonyl)amino-1-(N,N-isobutyl-4-aminobenzenesulfonyl)amino-2-(S)-hydroxy-4-phenylbutane; 4-amino-N-(2(R)-hydroxy-4-phenyl-3-(S)-(tetrahydrofuran-3-(S)-yloxycarbonylamino)butyl)-N-isobutylbenzenesulfonamide (alternatively known as VX 478 or 141W94) as shown as the structure of compound of formula (I) below (I)

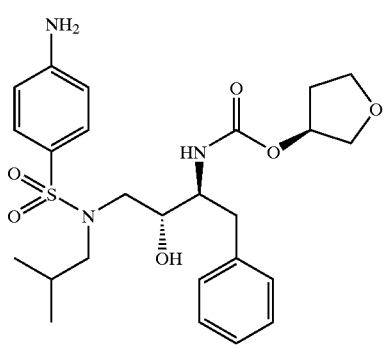

The compound of formula (I), disclosed in WO94/05639 and incorporated herein by reference, has been found to be especially effective as an inhibitor of HIV-1 and HIV-2. Particularly preferred is the compound of formula (I).

It may be that an HIV protease inhibitor has a high degree of potency against HIV but it is, of course, essential that when administered to a patient that the HIV protease inhibitor reaches the site of action at an amount and for a duration sufficient for a therapeutic effect to occur, but yet not to reach such levels that excessive and unavoidable toxic effects are present. Therefore in common with other drugs the bioavailability of the HIV protease inhibitor is determined so as to deduce the amount of drug needed to be administered to the patient in order to satisfy the above criteria.

A definition of "bioavailability" can be found in Pharmaceutical Sciences, Remington, 17th Ed., page 1424, quoted below.

"Bioavailability is an absolute term that indicates measurement of both the time (rate) and total amount (extent) of drug that reaches the general circulation from an administered dosage form".

There are many factors which affect the bioavailability of a drug. A drug must first go into solution prior to absorption and, therefore, a key factor is the dissolution rate of a drug. Typical of the class of drugs HIV protease inhibitors have poor physical characteristics of low solubility and wettability and accordingly their dissolution rate is low. Therefore, simple tablet or capsule formulations of such drugs will have a low bioavailability and need to be administered in much higher quantities in order to achieve a therapeutic effect.

Current formulations of HIV protease inhibitors for oral administration are in powder or tablet form. However, HIV protease inhibitors in these oral formulations are generally poorly soluble and, therefore, poorly bioavailable for the above reasons. For example, the aqueous solubility of the compound of formula (I) is only 0.095 mg/mL at room temperature and does not significantly vary with pH (FIG. 1). In addition, the compound of formula (I) is poorly wetted. Therefore, formulating the compound using standard formulary techniques is difficult and leads in any event to a formulation with low bioavailability.

Therefore, improvements in the bioavailability of HIV protease inhibitors is an important goal in this field offering many advantages, such as, lower quantities of drug administered to achieve the same therapeutic effect and fewer dosages required at less frequent intervals thereby improving patient compliance.

To avoid a dissolution rate limiting formulation and improve bioavailability we formulated the compound of formula (I) as a solution suitable for oral administration. We found that 10 mg/mL of the compound of formula (I) in Polyethylene Glycol 400 (PEG400) solution had an oral bioavailability of 25–30% (Table 1). However, at higher concentrations of the compound of formula (I) in PEG400 (250 mg compound of formula (I)/gram solution), the bioavailability dropped to half the value achieved with the 10 mg/mL solution and the maximal concentration (Cmax) achieved was also drastically reduced (Table 1).

Surprisingly, we have found that when the compound of formula (I) is administered as a solution comprising d-Alpha Tocopheryl Polyethylene Glycol 1000 Succinate (Vitamin E-TPGS) the bioavailability of the compound of formula (I) is greatly improved.

Vitamin E-TPGS is a water soluble form of vitamin E and has been recognised as an excipient to promote emulsification of lipophilic substances, acting as a non-ionic surfactant, and in improving the bioavailability of certain drugs.

In The Lancet, 1991. 338, 212–214 Sokol R. J. et al teaches that coadministration of Vitamin E-TPGS with cyclosporin improves the bioavailability of cyclosporin.

In WO95/31217 (Dumex Ltd) it is taught that tocopherols can be used as a solvents and/or emulsifiers of drugs substantially insoluble in water, in particular for the preparation of topical formulations. Use of Vitamin E-TPGS is specifically mentioned at pages 7–8 and 12 as an emulsifier for use in formulations containing high levels of α-tocopherol as the lipid layer. Examples of formulations for topical administration disclosed containing Vitamin E-TPGS, such as Examples 1 to 5, typically comprises a lipid layer (an α-tocopherol), the drug and Vitamin E-TPGS, in quantities of less than 25% w/w of the formulation, as an emulsifier. There is no reference to formulation of HIV protease inhibitors.

In WO96/36316 (Abbott Laboratories), which published after the priority date but before the filing date of this application, it is taught that Vitamin E-TPGS can be used for the enhanced delivery of lipophilic compounds as a self-emulsifying preconcentrate formulation comprising a) a lipophilic drug (a cyclosporin is specifically exemplified), b) vitamin E-TPGS and c) a lipophilic phase. Typical examples of formulations disclosed, such as Examples 2 and 4, contain less than 14% w/w Vitamin E-TPGS as an emulsifier, a lipid layer and the drug. There is no reference to formulation of HIV protease inhibitors.

We have now found that the bioavailability of an HIV protease inhibitor can be significantly enhanced by formulation as a liquid formulation comprising a water soluble tocopherol derivative, in particular Vitamin E-TPGS.

We surprisingly found that formulations comprising (a) an HIV protease inhibitor and (b) a water soluble tocopherol derivative in a ratio of from about 1:0.5 to about 1:10 w/w have advantageous properties in terms of bioavailability.

The present invention thus provides, in a first aspect, a pharmaceutical formulation for oral administration comprising a) an HIV protease inhibitor and b) a water soluble tocopherol derivative in a ratio of from about 1:0.5 to about 1:10 w/w.

We have further found that formulations comprising a) an HIV protease inhibitor b) at least 20% w/w of a water soluble tocopherol derivative such as Vitamin E-TPGS have good bioavailability even when the HIV protease inhibitor is present at high concentrations.

We have found that for formulations of HIV protease inhibitors and water soluble tocopherol derivatives a lipophilic phase is not needed thus reducing costs and making formulation more convenient. The absence of a lipophilic phase and the ability to dissolve the HIV protease inhibitor at much higher concentrations without adversely affecting bioavailability means that smaller, more convenient, cheaper and easier to manufacture formulations result.

The present invention thus provides, in a further or alternative aspect, a pharmaceutical formulation for oral administration comprising (a) an HIV protease inhibitor and (b) at least 20% of a water soluble tocopherol derivative in the absence of a lipophilic phase.

In a further alternative aspect, the present invention provides a pharmaceutical formulation for oral administration comprising (a) an HIV protease inhibitor and (b) at least 20% of a water soluble tocopherol derivative wherein the ratio of (a) to (b) is from about 1:0.5 to about 1:10 w/w.

Preferably the water soluble tocopherol derivative is Vitamin E-TPGS.

Preferably the formulations of the invention comprise from about 10% to about 60% w/w water soluble tocopherol derivative, preferably Vitamin E-TPGS, more preferably about 20% to about 50% such as about 30% to about 50% w/w, for example, about 30%.

Preferably the HIV protease inhibitor is the compound of formula (I).

The ratio of HIV protease inhibitor to water soluble tocopherol derivative in the formulations of the invention is preferably from about 1:0.5 to about 1:3, such as, for example, from about 1:0.67 to about 1:2.6 w/w, more preferably from about 1:1.3 to about 1:3.

Water soluble tocopherol derivatives, in particular Vitamin E-TPGS, exist at room temperature as waxy solids. Whereas the HIV protease inhibitor compound may be administered to a patient in the water soluble tocopherol derivative alone it is preferable that additional pharmaceutical excipients are added to improve the physical properties of the formulation, for example by the addition of a hydrophilic non-aqueous solvent miscible with the water soluble tocopherol derivative to achieve a flowable liquid more suitable for mass formulation as, for example, in a soft gelatine capsule. Furthermore, we have found that the addition of a hydrophilic non-aqueous solvent miscible with the water soluble tocopherol derivative enhances the solubility of the HIV protease inhibitor allowing further reduction of the volume of the formulation required to deliver an effective dose. Preferred pharmaceutically acceptable solvents are polyethylene glycol and propylene glycol. Polyvinyl pyrrolidones can also be used. The addition of polyethylene glycol and propylene glycol to a formulation of an HIV protease inhibitor in Vitamin E-TPGS results in a flowable liquid which may suitably be filled into a soft gelatine capsule and represents a preferred feature of the invention.

When the compound of formula (I) was formulated in a mixture of Vitamin E-TPGS, PEG400 and propylene glycol, the bioavailability of the compound of formula (I) was not affected adversely as compared to formulation in Vitamin E-TPGS alone.

According to a preferred embodiment, the present invention provides a pharmaceutical formulation for oral administration comprising (a) an HIV protease inhibitor (b) a water soluble tocopherol derivative and (c) a hydrophilic non-aqueous solvent miscible with said water soluble tocopherol derivative wherein the ratio of (a) to (b) is from about 1:0.5 to about 1:10 w/w.

Preferably the hydrophilic non-aqueous solvent is selected from polyethylene glycol, propylene glycol and polyvinyl pyrrolidinone. More preferably the hydrophilic non-aqueous solvent is a mixture of polyethylene glycol, such as polyethylene glycol 400, and propylene glycol. The amount of hydrophilic non-aqueous solvent in the formulations of the invention may be in the range of about 15% to about 95%, such as about 25% to about 60% w/w.

In a preferred aspect, the present invention provides a pharmaceutical formulation for oral administration consisting essentially of (a) an HIV protease inhibitor (b) Vitamin E-TPGS (c) polyethylene glycol and (d) propylene glycol.

In a further preferred aspect, the invention provides a pharmaceutical formulation consisting essentially of (a) 3S-[3R*(1R*, 2S*)]-[3-[[(4-aminophenyl)sulphonyl](2-methylpropyl)-amino]-2-hydroxy-1-phenylmethyl)propyl]carbamic acid, tetrahydro-3-furanyl ester, [3-(S)-N-(3-tetrahydrofuranyloxycarbonyl)amino-1-(N,N-isobutyl-4-aminobenzenesulfonyl)amino-2-(S)-hydroxy-4-phenylbutane (b) Vitamin E-TPGS (c) polyethylene glycol and (d) propylene glycol.

The formulations of the invention are preferably presented in the form of capsules, more preferably soft gelatin capsules.

Included in the invention are the pharmaceutically acceptable salts, esters, or salts of such esters of HIV protease-inhibiting compounds, particularly the compound of formula (I), or any other compound which, upon administration of a safe and therapeutically effective amount of the compound to a human subject, is capable of providing (directly or indirectly) the antivirally active metabolite or residue thereof.

HIV protease-inhibiting compounds can be prepared as disclosed in WO95/24385, WO94/13629, WO92/16501, WO95/16688, WO94/13085, WO/US94/12562, US93/59038, EP 541168, WO94/14436, WO95/09843, WO95/32185, WO94/15906, WO94/15608, WO94/04492, WO92/

08701, WO95/32185, U.S. Pat. No. 5,256,783; 5,475,136; 5,461,067; 5,484,926; 5,476,874; 5,475,027; 5,482,947; and 5,475,013 which are incorporated herein by reference.

Compounds of Formula (I) may be prepared as disclosed in WO94/05639, which is incorporated herein by reference.

The water soluble tocopherol derivatives may be prepared by appropriate esterification procedures. Suitable procedures will be readily apparent to those skilled in the art. For example, Vitamin E-TPGS may be prepared by the esterification of polyethylene glycol 1000 to the acid group of crystalline d-alpha tocopheryl acid succinate as disclosed in U.S. Pat. Nos. 2,680,649 and 5,234,695.

As used herein, the term "solvent" means a solvent or cosolvent which is pharmaceutically or medicinally acceptable and which will dissolve an HIV protease inhibiting compound to form a solution and is not substantially destructive of the capsule shell.

Polyethylene glycols containing 300 to 1000 polyethylene glycol monomer units ($CH_2CH_2O$) can advantageously be used as solvents and polyethylene glycols having average molecular weights between 300 to 1000 and containing about 300 to 400 ethylene glycol monomer units as above may advantageously be used as solvents.

Other solvents or cosolvents which may also be suitable include, but are not limited to, propylene glycol, alcohol, glycerin, and sorbitol. Concentrations of solvents or co-solvents may suitable be in the range of 0.1% to 10%. In addition 0–10% water may be used as a co-solvent.

As used herein, the term lipophilic phase denotes one or more hydrophobic components such as, for example, fatty acid esters of glycerol, fatty acid esters of propylene glycol and vegetable oil.

Where the formulations of the invention are presented as capsules, the capsule shell may suitably be made of gelatin and may include plasticizers such as anidrisorb, glycerin or sorbitol, water, preservatives, coloring agent(s), and opacifying agent(s). Reference may be made to Remington's Practice of Pharmacy, Martin and Cook, Twelfth Edition, Pages 467 under the heading Elastic Capsules to page 469 for a description of gelatin capsules rapidly dissolvable in the gastrointestinal tract and the manufacture of such capsules, all of which are incorporated by reference herein. Reference may also be made to U.S. Pat. No. 2,899,361 as well as U.S. Pat. No. 2,928,128 for a description of soft gelatin capsules and their manufacture, both of said patents being incorporated herein by reference hereto. In addition reference may also be had to the book "The Theory and Practice of Industrial Pharmacy" by Lackman, Lieberman and Kanig (1970) pages 359–389 published by Lea and Febiger, Philadelphia, Pa. for a discussion of soft gelatin capsule technology said text pages 359–389 being incorporated herein by reference hereto.

The capsules of this invention may be of any shape, suitably the capsules may be elongated such as ellipsoidal, oval or cylindrical with rounded ends. A range of about 10 to 1500 mg of the compound of formula (I) may suitably be used. Preferably the capsules may contain 25 mg, 50 mg,150 mg or 200 mg of the compound of formula (I). Particularly, each capsule contains the compound of formula (I) in solution at a concentration of 10 to 1000 mg/mL with a concentration of 25 to 500 mg/mL being most preferred. As used herein, concentration means mg of the compound of formula (I)/mL of solution. The soft gelatin capsule may be chosen from those available from various manufacturers to hold the volume of the following examples to provide the concentration set forth therein. Preferably, the capsules are Size No. 12 oblong, or size No. 3 oval, white opaque soft gelatin capsules manufactured by R P Scherer, North America.

A preferred formulation according to the invention comprises an HIV protease-inhibiting compound (preferably a compound of formula (I)), in the amount of from about 1% to about 50% by weight of the total solution, and Vitamin E-TPGS in the amount of from about 5% to about 100% by weight of the total solution, polyethylene glycol in the amount of from about 15% to about 95% by weight of the total solution and propylene glycol in the amount of from about 0.1% to 10% by weight of the total solution. The formulation may optionally contain water in the amount of from about 0% to 10%.

As used herein the term "therapeutically effective amount" of the compound of formula (I) means one or more capsules of the type disclosed herein, with each capsule preferably containing 25 mg, 50 mg, 150 mg or 300 mg of the compound of formula (I). For initial treatment of patients, a dose of about 100 to 3000 mg of the compound of formula (I) followed by about 100 mg to 5000 mg of the compound of formula (I) may be used. Thereafter maintenance doses of 100 to 5000 mg of the compound of formula (I) may be administered depending on the patient. A suitable dosage regimen may be, for example, 1200 mg of the compound of formula (I) twice daily.

The formulations according to the invention may be presented in various forms adapted for direct oral administration including liquid forms, for example, syrups, suspensions, or solutions. The formulations, according to the invention, may include other pharmaceutically acceptable carriers as excipients conventionally used in such formulations. Thus, for example, syrups may include sugar syrup, sorbitol or hydrogenated glucose syrup or artificial sweeteners such as aspartame, sodium saccharin, acesulfame K, etc. Suspensions may include methylcellulose, microcrystalline cellulose, carmellose sodium or dispersible cellulose. Solutions may include liquid glucose, laevulose or xylitol.

The formulations of the present invention may be made using methods and techniques that are commonly employed in preparing preparations within the pharmaceutical industry.

The formulations according to the invention may be prepared in conventional manner, for example, by appropriate mixing of the ingredients in one or more vessels, the ingredients being dissolved or suspended using established pharmaceutical techniques. An HIV protease-inhibiting compound may be dissolved in the liquefied emulsifier-solvent mixture which has been heated to approximately 65° C. to facilitate dissolution. After the compound is completely solubilised, propylene glycol may be added to the resulting solution. The final solution, a clear flowable liquid between 28–35° C., may suitably be filled into soft gelatin capsules. Such a formulation when dissolved in water forms a clear solution with an improved bioavailability.

In the formulations according to the invention, the amount required of the compound of formula (I) will depend upon a number of factors including the severity of the condition to be treated and the age and condition of the recipient and will ultimately be at the discretion of the attendant physician. In general, however, a suitable, effective dose may be in the range of 5 to 100 mg/kg body weight of recipient per day, advantageously 8 to 70 mg/kg body weight and preferably 8 to 50 mg/kg body weight. The desired dose may preferably be presented at one, two, three, four or more sub-doses administered in unit dosage forms, for example, containing 25 to 500 mg of active ingredient per unit dosage form.

The formulations, according to the invention, may be used for the treatment or prophylaxis of human retroviral infections including HIV infections, and the consequent clinical conditions resulting from such infections, for example, AIDS, ARC, progressive generalised lymphadenopathy (PGL) and HIV-seropositive and AIDS-antibody-positive conditions.

The formulations according to the invention may be employed in medical therapy in combination with other therapeutic agents suitable in the treatment of HIV infections, such as nucleoside reverse transcriptase inhibitors for example zidovudine, zalcitabine, lamivudine, didanosine, stavudine, 5-chloro-2',3'-dideoxy-3'-fluorouridine and (2R,5S)-5-fluoro-1-[2-(hydroxymethyl)1,3-oxathiolan-5-yl]cytosine; non-nucleoside reverse transcriptase inhibitors for example nevirapine, TIBO, and A-APA; HIV protease inhibitors for example saquinavir, indinavir and ritonavir; other anti-HIV agents for example soluble CD4; immune modulators for example interleukin II, erythropoetin, tucaresol; and interferons for example α-interferon.

The components of such combination therapy may be administered simultaneously, in either separate or combined formulations or at different times, e.g. sequentially such that a combined effect is achieved.

BRIEF DESCRIPTION OF THE FIGURES

FIG. 1 shows the solubility of the compound of formula (I) with varying pH.

The following examples are included to illustrate the present invention but are not intended to limit the reasonable scope thereof.

EXAMPLE 1

A liquid formulation was prepared as follows:
1) Composition

| Ingredient | Quantity (mg/capsule) |
|---|---|
| Compound of formula (I) | 150.0 |
| Vitamin E-TPGS | 400.0 |
| Polyethylene Glycol 400 NF | 200.5 |
| Propylene Glycol USP | 39.5 |

2) Method of Preparation

Four (4) kilograms (kg) of Vitamin E-TPGS (obtained from Eastman Chemical Co.) was heated at 50° C. until liquefied. To the liquefied Vitamin E-TPGS, 2.005 kg of polyethylene glycol 400 (PEG400) (low aldehyde, <10 ppm, obtained from Union Carbide or Dow Chemical Co.) heated to 50° C. was added and mixed until a homogenous solution was formed. The resultant solution was heated to 65° C. 1.5 kg of the compound of formula (I) was dissolved in the liquefied solution of Vitamin E-TPGS and PEG400. 0.395 kg of propylene glycol at room temperature was added and mixed until a homogenous solution was formed. The solution was cooled to 28–35° C. The solution was then de-gassed. The mixture was preferably encapsulated at 28–35° C. at a fill weight equivalent to 150 mg of volatiles-free compound, into Size 12 oblong, white opaque soft gelatin capsules using a capsule filling machine. The capsule shells were dried to a constant fill moisture of 3–6% water and a shell hardness of 7–10 newtons, and placed in a suitable container.

EXAMPLE 2

Pharmacokinetics of the Compound of Formula (I) in Rats and Beagle Dogs

The pharmacokinetics of the compound of formula (I) after intravenous and oral administration was assessed in Hsd: Sprague Dawley SD rats after doses of 10, 24.1, and 50 mg/kg, dissolved in PEG400. Pharmacokinetics were also conducted with D-alpha tocopheryl PEG1000 Succinate (TPGS) and mixtures of Vitamin E-TPGS, PEG400, and propylene glycol in Hsd rats and beagle dogs.

Rat Pharmacokinetics

The compound of formula (I) was administered individually to groups of four cannulated Hsd rats by intravenous injection at doses of 10 and 50 mg/kg or gavage at doses of 10, 24.1, and 50 mg/kg dissolved in PEG400. Four other animals received individual capsules containing the compound of formula (I) in solution with PEG400 and Vitamin E-TPGS at an average dose of 11 mg/kg. Blood samples were drawn at various times from 2 min to 7 hr post-dose. The principal pharmacokinetic parameters of the compound of formula (I) are summarized in Table 1.

Beagle Dog Pharmacokinetics

The principal pharmacokinetic parameters of the compound of formula (I) in beagle dogs are summarized in Table 2.

TABLE 1

Pharmacokinetics of the compound of formula (I) in rats with different formulations

| Formulation % w/w | dose/route (mg/kg) | Cmax ($\mu$M) | Tmax (hr) | AUC ($\mu$M.hr) | F |
|---|---|---|---|---|---|
| 10 mg/mL (I) in a PEG400 solution | 10 mg/kg iv | 42.6 ± 12.2 | 2 min[a] | 9.0 ± 1.0 | |
| | po | 2.6 ± 1.3 | 0.4 ± 0.2 | 2.6 ± 0.3 | 29% |
| 10 mg/mL (I) in a PEG400 solution | 50 mg/kg iv | 107 ± 11 | 2 min[a] | 71.5 ± 43 | |
| | po | 7.9 ± 3.4 | 0.9 ± 0.2 | 18.2 ± 8.6 | 25% |
| 250 mg/gm (I) in a PEG400 solution | 24.1 mg/kg po | 0.8 ± 0.3 | 2.5 ± 2.2 | 2.5 ± 0.8 | 11.6%[b] |
| 21.8% (I) 63.3% Vit E-TPGS 14.9% other buffer ingredients | 11 mg/kg po | 1.4 ± 0.7 | 2.3 ± 2.3 | 2.6 ± 1.2 | 26.3%[b] |
| 25% (I) 60.75% Vit E-TPGS 14.25% other buffer ingredients | 21 mg/kg po | 2.7 ± 1.4 | 2.7 ± 2.0 | 5.2 ± 2.5 | 27.5%[b] |
| 23.2% (I) 27.2% PEG400 44.8% Vit E-TPGS 4.8% Propylene Glycol | 11 mg/kg po | 2.8 ± 1.1 | 1.1 ± 0.6 | 4.2 ± 1.6 | 42.4%[b] |

Each set of values are averages ± standard deviation

TABLE 1-continued

Pharmacokinetics of the compound of formula (I) in rats with different formulations

| Formulation % w/w | dose/route (mg/kg) | Cmax (μM) | Tmax (hr) | AUC (μM.hr) | F |
|---|---|---|---|---|---|

[a]earliest time taken, concentration not extrapolated to origin
[b]F value normalised with iv 10 mg/kg data
Cmax: The maximum concentration observed, were calculated from individual observed levels.
Tmax: the time the maximum concentration observed, were calculated from individual observed levels.
AUC: Area under the concentration time curve, were determined for individual animals.
F, Bioavailability determined by AUC po/AUC iv
All percentages are based on w/w basis

TABLE 2

Pharmacokinetics of the compound of formula (I) in Beagle dogs Different formulations with 150 mg the compound of formula (I) per capsule

| Formulation % w/w | Cmax (μM) | Tmax (hr) | AUC (μM.hr) | dose (mg/kg) |
|---|---|---|---|---|
| 21.8% (I) 63.3% Vit E-TPGS 14.9% other buffer ingredients | 11.1 ± 1.8 | 1.6 ± 0.9 | 29.3 ± 5.3 | 15.3 |
| 23.2% (I) 27.2% PEG400 44.8% Vit E-TPGS 4.8% Propylene Glycol | 13.6 ± 2.3 | 1.1 ± 0.6 | 32.9 ± 7.4 | 15.3 |
| 20.0% (I) 39.0% PEG400 39.0% Vit E-TPGS 2% Propylene Glycol | 13.1 ± 4.4 | 0.6 ± 0.4 | 30.5 ± 11.2 | 15.3 |

Each set of values are averages ± standard deviation
Cmax: The maximum concentration observed, were calculated from individual observed levels.
Tmax: the time the maximum concentration observed, were calculated from individual observed levels.
AUC: Area under the concentration time curve, were determined for individual animals.
All percentages are based on w/w basis

TABLE 3

Pharmacokinetic parameter estimates (average ± SD; n = 3) after oral administration of the compound of Formula (I) (300 mg) to dogs.

| Formulation | Cmax (μg/mL) | Tmax (hr) | $t_{1/2}$ (h) | AUC (0 to 24 h) (h × μg/mL) |
|---|---|---|---|---|
| Dry Fill | 0 | 0 | 0 | 0 |
| PVP suspension[a] | 0.03 ± 0.01[b] | 3.0 ± 0 | 1.2 ± 0.1 | 0.12 ± 0.04[b] |
| PEG400 | 3.85 ± 1.25 | 1.1 ± 0.9 | 4.2 ± 1.7 | 12.2 ± 1.46 |
| 20% Vit E-TPGS | 5.41 ± 0.69 | 1.7 ± 0.6 | 3.6 ± 0.8 | 22.1 ± 4.52 |
| 25% Vit E-TPGS | 5.03 ± 0.44 | 1.7 ± 0.6 | 2.0 ± 0.8 | 20.6 ± 4.85 |
| 30% Vit E-TPGS | 8.24 ± 0.12 | 1.3 ± 0.6 | 2.0 ± 0.7 | 23.5 ± 4.97 |
| 40% Vit E-TPGS | 6.92 ± 0.94 | 1.7 ± 0.6 | 1.9 ± 0.6 | 24.4 ± 4.55 |
| 50% Vit E-TPGS (CTM) | 7.63 ± 1.46 | 1.7 ± 0.6 | 2.5 ± 1.3 | 26.8 ± 8.27 |

[a](n = 1)
[b]Normalized to 300 mg dose

What is claimed is:

1. A pharmaceutical formulation possessing unexpectedly enhanced bio-availability, comprising:
   a) 3S-[3R*(1R*,2S*)]-[3-[[4-aminophenyl)sulphonyl](2-methylpropyl)-amino]-2-hydroxy-1-phenylmethyl)propyl]carbamic acid, tetrahydro-3-furanyl ester,
   b) a water soluble tocopherol derivative, and
   (c) a hydrophilic non-aqueous solvent miscible with said water soluble tocopherol derivative.

2. A pharmaceutical formulation as claimed in claim 1, comprising at least 20% of the water soluble tocopherol derivative.

3. A pharmaceutical formulation as claimed in claim 1, wherein the ratio of (a) to (b) is from about 1:0.5 to about 1:3 w/w.

4. A pharmaceutical formulation as claimed in claim 1, wherein the water soluble tocopherol derivative is Vitamin E-TPGS.

5. A pharmaceutical formulation as claimed in claim 1, in the form of a capsule.

6. A pharmaceutical formulation as claimed in claim 1, comprising 3S-[3R*(1R*, 2S*)]-[3-[[4-aminophenyl)sulphonyl](2-methylpropyl)-amino]-2-hydroxy-1-phenylmethyl)propyl]carbamic acid, tetrahydro-3-furanyl ester in an amount of about 10 to about 1500 mg.

7. A pharmaceutical formulation as claimed in claim 1, wherein the hydrophillic non-aqueous solvent is a mixture of a polyethylene glycol and propylene glycol.

8. A pharmaceutical formulation as claimed in claim 1, in the form of a solution.

9. A pharmaceutical formulation as claimed in claim 1, comprising 3S-[3R*(1R*, 2S*)]-[3-[[4-aminophenyl)sulphonyl](2-methylpropyl)-amino]-2-hydroxy-1-phenylmethyl)propyl]carbamic acid, tetrahydro-3-furanyl ester in an amount of about 10 to about 1500 mg.

10. The pharmaceutical formulation of claim 1, wherein the water soluble tocopherol derivative is Vitamin E-TPGS.

11. A pharmaceutical formulation, comprising:
   a) 3S-[3R*(1R*,2S*)]-[3-[[4-aminophenyl)sulphonyl](2-methylpropyl)-amino]-2-hydroxy-1-phenylmethyl)propyl]carbamic acid, tetrahydro-3-furanyl ester,
   b) from about 10% to about 60% w/w of a water soluble tocopherol derivative, and
   (c) a hydrophilic non-aqueous solvent miscible with said water soluble tocopherol derivative,
   wherein the ratio of (a) to (b) is from about 1:0.5 to about 1:10 w/w, and wherein said formulation possesses unexpectedly enhanced bioavailability.

12. A pharmaceutical formulation as claimed in claim 11, in the form of a soft gelatin capsule.

13. A pharmaceutical formulation, comprising:
   (a) 3S-[3R*(1R*,2S*)]-[3-[[4-aminophenyl)sulphonyl](2-methylpropyl)-amino]-2-hydroxy-1-phenylmethyl)propyl]carbamic acid, tetrahydro-3-furanyl ester, (b) Vitamin E-TPGS, (c) polyethylene glycol, and (d) propylene glycol, and wherein said formulation possesses unexpectedly enhanced bioavailability.

14. A pharmaceutical formulation as claimed in claim 13, in the form of a soft gelatin capsule.

15. The pharmaceutical formulation according to claim 13, which comprises from about 10% to about 60% w/w of Vitamin E-TPGS.

16. The pharmaceutical formulation according to claim 13, wherein said formulation is a flowable liquid.

17. The pharmaceutical formulation according to claim 13, wherein said formulation is formulated for oral administration.

18. A pharmaceutical formulation, comprising:

(a) 3S-[3R*(1R*,2S*)]-[3-[[4-aminophenyl)sulphonyl](2-methylpropyl)-amino]-2-hydroxy-1-phenylmethyl)propyl]carbamic acid, tetrahydro-3-furanyl ester in an amount from 1% to 50% w/w;

(b) a water soluble tocopherol derivative in an amount from about 10% to about 60% w/w; and (c) a hydrophilic non-aqueous solvent miscible with the water soluble tocopherol derivative in an amount from about 15% to about 95%, wherein, the hydrophilic non-aqueous solvent is a polyethylene glycol, propylene glycol, polyvinyl pyrrolidone, or a combination thereof; and wherein said formulation possesses unexpectedly enhanced bioavailability.

19. A pharmaceutical formulation according to claim 18, wherein the water soluble tocopherol derivative is Vitamin E-TPGS.

20. The pharmaceutical formulation according to claim 18, wherein said formulation is in the form of a soft gelatin capsule.

21. A pharmaceutical formulation for oral administration, comprising:

(a) about 19% w/w of 3S-[3R*(1R*,2S*)]-[3-[[4-aminophenyl)sulphonyl](2-methylpropyl)-amino]-2-hydroxy-1-phenylmethyl)propyl]carbamic acid, tetrahydro-3-furanyl ester, (b) about 51% w/w of Vitamin E-TPGS, (c) about 25% w/w of polyethylene glycol, and (d) about 5% w/w of propylene glycol, and wherein said formulation possesses unexpectedly enhanced bioavailability.

* * * * *